United States Patent [19]

Allington

[11] 4,225,290
[45] Sep. 30, 1980

[54] PUMPING SYSTEM

[75] Inventor: Robert W. Allington, Lincoln, Nebr.

[73] Assignee: Instrumentation Specialties Company, Lincoln, Nebr.

[21] Appl. No.: 13,986

[22] Filed: Feb. 22, 1979

[51] Int. Cl.³ ............................................ F04B 49/00
[52] U.S. Cl. ........................................ 417/18; 318/48
[58] Field of Search ........................ 417/18, 19, 20, 21, 417/22, 23, 38; 318/48, 34, 41, 66

[56] References Cited

U.S. PATENT DOCUMENTS

| | | | |
|---|---|---|---|
| 3,855,129 | 12/1974 | Abrahams | 417/38 |
| 3,985,467 | 10/1976 | Lefferson | 417/20 |
| 4,024,864 | 5/1977 | Davies | 417/20 |
| 4,108,574 | 8/1978 | Bartley | 417/19 |
| 4,180,375 | 12/1979 | Magnussen | 417/22 |

Primary Examiner—Robert W. Jenkins
Attorney, Agent, or Firm—Vincent L. Carney

[57] ABSTRACT

An improved chromatographic pump control circuit for compensating for pulsation in pump flow over a wide range of flow-rates and pressures and for providing improved protection against pump pressure and motor torque fault conditions. The control circuit is coupled to a pump motor to provide motor speed-up during the repressurization portion of the pump cycle as a function of the set point pump flow rate. The circuit also includes a summing circuit for developing a repressurization signal based on the flow-rate and detected pressure. The signal is coupled to compensate for pulsation by controlling the duration of repressurization with respect to both pressure and the set point of the flow rate. The circuit is additionally coupled to sense pump pressure and motor torque to initiate alarm and pump shutdown during high and low pressure and motor over-torque fault conditions.

26 Claims, 7 Drawing Figures

Fig. 3

PUMPING SYSTEM

BACKGROUND OF THE INVENTION

The present invention relates to pump motor control circuitry and more particularly to improved circuitry for compensating for pulsations in pump output flow in chromatographic systems.

Chromatography is a technique for separating a mixture of components, known as a sample, by distributing the sample in dynamic equilibrium between two phases in ratios characteristic of each component. The sample is normally dissolved in a flowing mobile phase and forced through a stationary phase, as by pumping, to cause each component of the sample to migrate through the stationary phase at a characteristic rate. After a period of time, the migration results in the separation of the components into individual zones which can be detected by a detector to identify individual components.

In order to provide for resolution of the components within the sample, various characteristics of the system (e.g., flow-rate, chemical composition, temperature) can be changed to improve system performance. Of particular importance is the ability to maintain a relatively pulse free pump output flow for any particular system flow-rate. In operation, a system may be controlled to provide a constant or variable flow-rate with a single pump, constant flow-rate with a programmed chemical composition in a gradient system, a constant chemical composition with a programmed flow-rate in a gradient system, or a programmed flow-rate and chemical composition in a gradient system. In each case, however, the sensitivity of detection and quantitation of the zones depends upon the noise level of the detector. Since detector noise is aggravated by pulsations in the flow-rate, the sensitivity of analysis, and thus the resolution and reproducibility of system performance depends on the capability of maintaining the pump output flow relatively free of pulsations caused by pump refill and repressurization over the operating range of flow-rates and pressures for the chromatographic system.

In the prior art various techniques have been proposed to minimize or eliminate pulsations in pump output flow. In one such system, pump speed is increased during refill and repressurization and pump pressure, detected as a function of motor torque, is used to produce a signal for controlling the length of the piston stroke through which the motor is speeded up for rapid repressurization. While in this arrangement some compensation is provided, the control fails to provide sufficient compensation over the desired range of flow-rates and pressures in a chromatographic system. Such system fails to provide tracking for repressurization as a function of varying flow-rates. Thus, if the compensation circuit is set to minimize pump flow pulsations at low flow-rates, the pulsations will be under-compensated at high flow-rates and high pressures. More specifically, as the flow-rate setting is increased, the average output flow-rate actually drops off at high flow-rates since the time interval for actual physical repressurization of the pump, as determined by the prior art circuitry, tends to become a larger fraction of the pumping cycle as the flow-rate increases. In addition, since the repressurization signal is derived from a measure of motor torque rather than actual pressure, pulse compensation does not accurately track system pressure.

In the noted prior art system, the detected motor torque is also used to indicate fault conditions due to over and under pressures at which the chromatographic system will not properly operate. Such system, however, provides circuitry which does not enable the setting of accurate reference limits to control alarm and pump shutdown during fault conditions. In addition, since the motor torque is used as a measure of pressure, the system may respond to torque conditions causing alarm and pump shutdown which are not actual pressure faults. In still other instances, the circuitry is not capable of detecting pressure fault conditions that should signify alarm and pump shutdown.

Accordingly, the present invention has been developed to overcome the shortcomings of the above known and similar techniques and to provide pump control circuitry for allowing improved pulse compensation and fault detection in chromatographic systems.

SUMMARY OF THE INVENTION

It is therefore an object of the present invention to provide a pump control circuit for compensating for flow pulsations over a wide range of flow-rates.

Another object of the invention is to provide pump control circuitry for providing improved pulse compensation in output flow over a range of operating pressures and particularly at low output pressures.

A further object of the invention is to provide a pump control circuit which provides improved tracking and linearity of pulse compensation with respect to flow-rate.

Still another object of the invention is to provide a pump control circuit which controls pump speed during repressurization as a function of flow-rate and pressure.

A still further object of the invention is to provide a pump control circuit that may be used to reduce flow pulsations in both single pump and gradient chromatographic systems.

Yet another object of the invention is to provide a pump control circuit in a chromatographic system which provides an accurate detection of pressures above and below present limits to produce alarm and pump shutdown.

Still another object of the invention is to provide a pump control circuit in a chromatographic system which provides alarm and pump shutdown in response to a pump motor over-torque condition.

In order to accomplish these and other objects, a pump control circuit is coupled to receive a signal indicative of the output pressure of the mobile phase in a chromatographic system. The output pressure is smoothed to be proportional to the actual delivery stroke pressure and summed with a signal representing the flow-rate setting of the pump. The combined signal is coupled to a comparator to control the volumetric duration of motor speed-up during the repressurization interval to provide for pulse compensation in the pump output flow. The summing circuit includes an adjustment capable of varying the signal baseline level to compensate with respect to both flow-rate and actual pressure. A signal indicative of actual pressure is also provided to individual comparator circuits which detect pressure above and below reference values set to be proportional to high and low pressure limits. When an output is provided from the comparator circuits, alarm and pump shutdown controls are initiated to stop system operation. In addition, an over-torque signal is derived by sensing armature current above a preselected value. The over-torque signal is also coupled to indicate pump fault and cause alarm and motor shutdown.

BRIEF DESCRIPTION OF THE DRAWINGS

Still other objects, advantages, and novel features of the invention will become apparent from the following detailed description when considered with the accompanying drawings wherein.

DETAILED DESCRIPTION OF THE PREFERRED EMBODIMENT

Figure 1:
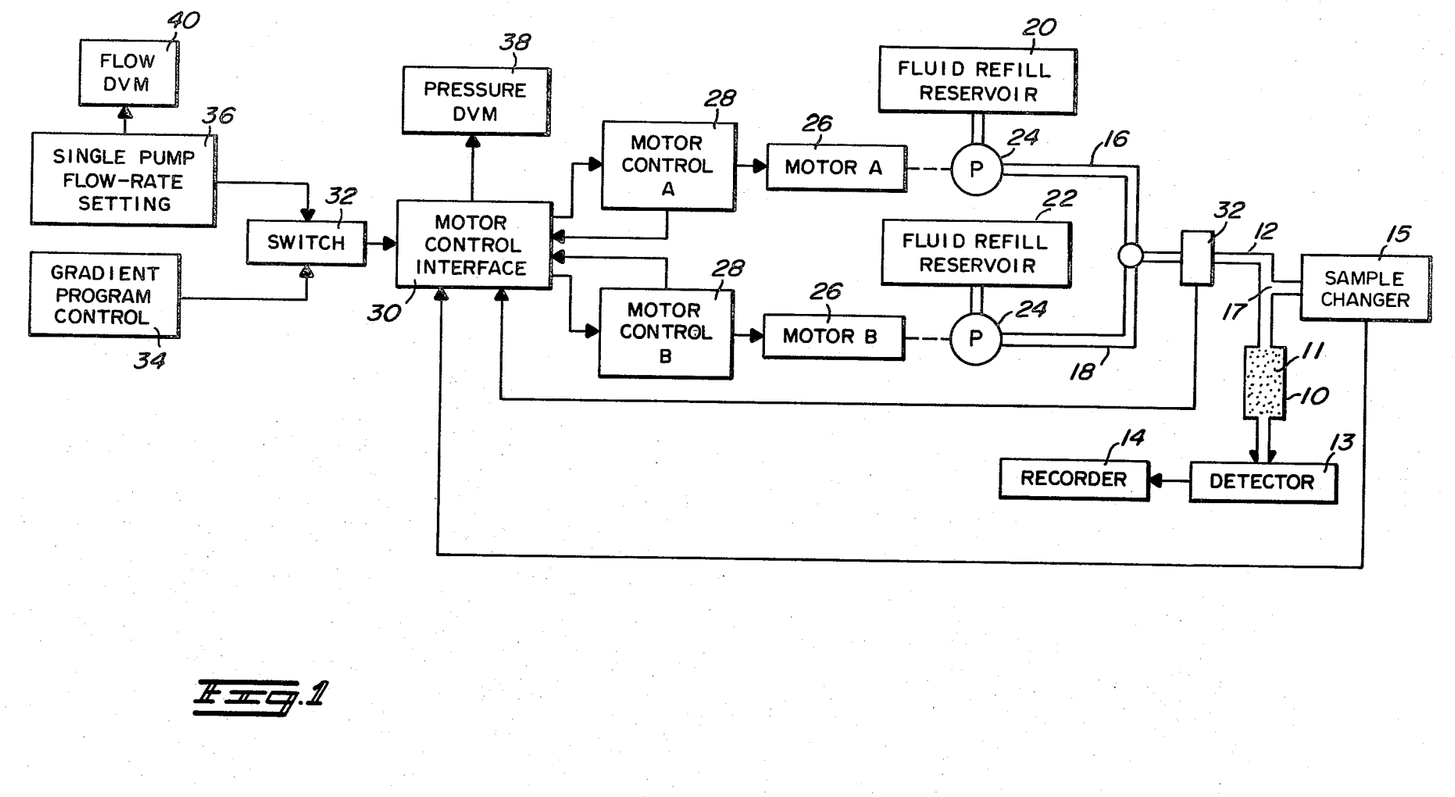
FIG. 1 is a block diagram of a chromatographic system employing the pump control circuitry in accordance with the present invention.

Referring now to FIG. 1, a schematic diagram shows a chromatographic system incorporating the features of the present invention wherein like numerals are used to identify like elements throughout the drawings. In the present instance, the invention will be described with reference to a liquid chromatographic system which is capable of providing gradient elution and flow programming as is well known in the art. It is to be understood, however, that the teachings of the present invention are equally applicable to other well known applications of high pressure metering pumps.

Generally, the system includes a typical chromatographic column 10 packed with a stationary phase 11 and supplied with column eluent that contains solutes dissolved in a mobile phase which is forced through the column 10 to the detector 13. Multiple sample mixtures containing the solutes are located in sample changer 15. The samples removed from the sample changer and injected into the stream of mobile phase by conventional means includes sample injection valve 10. The detector is responsive to individual solutes dissolved in the mobile phase and provides an output signal which is displayed on a strip chart recorder 14 or any other similar recording device. The detector signal responds to flow-rate fluctuations as well as solute concentration. Hence, for maximum solute and detection sensitivity, the flow-rate must be free of fluctuations. After passing through the detector 13, the eluent is collected by a conventional fractional collector (not shown) which may include a plurality of vials disposed in a rotating rack that is controlled in synchronization with the gradient to receive a portion of the eluent containing individual components of the solute as they pass through the detector at different times.

In the present embodiment, the mobile phase in conduit 12 is provided as a mixture of mobile phases A and B supplied through conduits 16 and 18 from fluid refill reservoirs 20 and 22 respectively. Each reservoir includes a mobile phase of a particular chemical composition having the selected solute dissolved therein and provided to the conduits 16 and 18 by individual pumps 24 driven by motors 26. The motors are controlled by separate motor control circuits 28 which are in turn controlled by a motor control interface 30. The motor control 28, motor 26, and pump 24, in the circuit coupled to deliver mobile phase A, are intended to be of identical construction to the corresponding elements in the circuit coupled to deliver mobile phase B. Accordingly, subsequent reference to the construction and operation of the elements 24, 26, and 28 will necessarily apply to those corresponding elements coupled to deliver both mobile phases A and B.

In accordance with the present invention, the motor control interface 30 is coupled to receive an input signal from a pressure transducer switch 32 (FIGS. 1 and 3) positioned to provide an indication of the actual pressure in the conduit 12. In addition, the motor control interface 30 is coupled through switch 32 to receive signals from a conventional gradient program control 34 or from a single pump or gradient chromatographic system. When the system is operated in the single pump mode, the flow-rate setting is coupled to a flow-digital voltmeter 40 for providing a visual output of the flow-rate. The interface control also receives signals from the sample changer 15 to provide for automatic sequential injection and chromatographic analysis of multiple samples, and provides an output to pressure digital voltmeter 38 for monitoring system pressure. These and other features of the motor control interface control 30, including pulsation compensation, pressure fault detection and display, and pump shutdown, will be more particularly described in connection with FIGS. 2 and 3 below.

In the prior art, the pumps selected to supply the mobile phase often exhibit pulsations in the output flow-rate and pressure during refill and repressurization which adversely affect system performance. The pulsations in the output flow are created during the time that the pump piston retracts to refill its chamber and during the first part of the delivery stroke of the piston. At these times, the output flow stops until the pressure in the pump chamber rises slightly higher than the outlet pressure so that liquid can flow through a check valve at the pump outlet. These two contiguous zero-flow periods are known as refill and repressurization times and the same result in residual pulsation in the pump outlet flow which, if uncompensated, get worse at high pressures. In order to reduce such pulsations, the prior art employs a drive cam for the pump piston that has a linear spiral contour and rapid return. Thus, if the speed of the drive motor is constant, the pump output flow-rate will be constant during the delivery stroke but the cam will still act to return the piston at a faster rate during refill to reduce the time period (and therefore the pulsations) for refill and repressurization.

In connection with the above-noted cams, the prior art systems have also employed compensating circuitry designed to speed up the motor during refill and repressurization to further reduce their effect in producing pulsations. As a general rule, however, such circuitry has produced a compensation signal based on a presumed pressure derived from motor torque and which does not provide for adequate tracking for repressurization compensation as a function of varying flow rates. Thus, while both the cam and compensation circuitry have improved output flow, prior art circuits have still been limited in the maximum compensation and linearity that could be attained over the operating ranges for pump flow-rates and pressures, particularly in gradient chromatographic systems.

Figure 2:
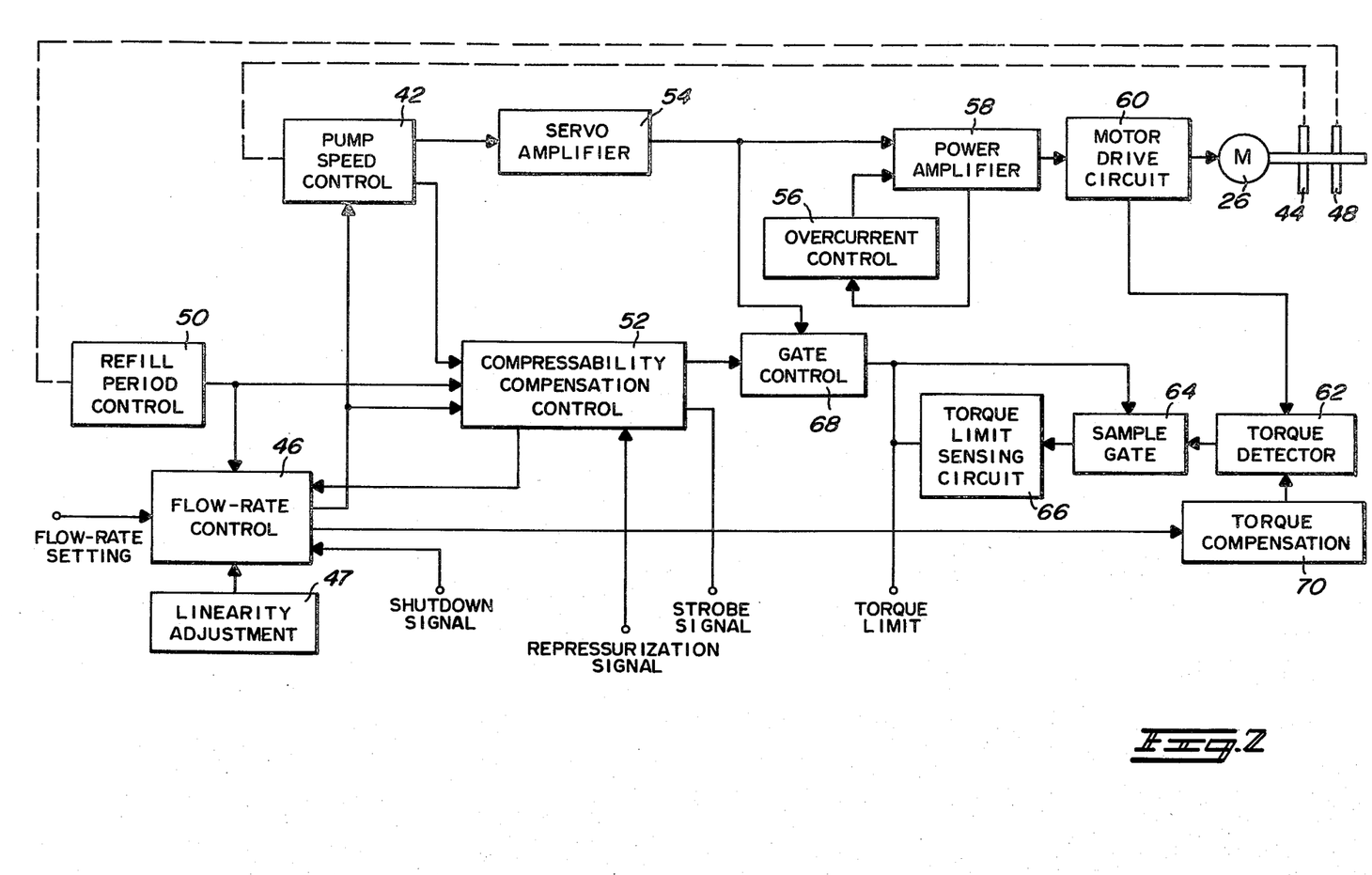
FIG. 2 is a block diagram schematically showing the functional operation of the motor control shown in FIG. 1.

Turning now to FIG. 2, a block diagram shows an arrangement suitable for use as either of the motor controls A or B indicated at 28 in FIG. 1, when operated in conjunction with the motor control interface 30, produces improved flow pulsation compensation and linearity of operation. The circuit also provides for the generation of an over-torque signal representing a fault condition requiring pump shutdown.

In the present example, the motor 26 is a low inertia disc-armature DC motor controlled to operate both thermally and dynamically by the circuit 28 as a simple DC velocity servo system. The motor should have low inertia to provide rapid velocity response. Basically, the motor is controlled to provide cyclic motor speeds that will produce the desired flow-rate within the operating pressure range while minimizing the effect of pulsations during refill and repressurization. The motor is additionally controlled to respond to a fault due to an over-torque condition as may be detected by the circuit 28.

In order to control motor speed during pump delivery, refill, and repressurization, a signal is developed by pump speed control 42 which is indicative of the desired speed of the motor during each part of its operating cycle. The signal is developed by combining a flow-rate signal from control 46 and a signal representing actual motor speed. The actual speed signal is provided by a tachometer disc 44 located on the shaft of motor 26 and mechanically coupled to pump speed control unit 42 to produce a signal indicative of actual motor speed. The flow-rate signal is developed by control 46 in response to various inputs designed to control motor speed during each of the delivery, refill, and repressurization periods of the pump cycle. Thus, during the delivery stroke, control 46 is construed to produce an output control signal from 42 which will produce a pump speed corresponding to the flow-rate setting input provided to control 46 from motor control interface 30 (not shown in FIG. 2) as will be later described. During the refill portion of the pump cycle, a disc 48 located on the output of the motor shaft and mechanically coupled to refill period control 50, causes the generation of a signal output at control 50 which, when coupled to control 46, provides a signal to control 42 to speed up the motor. The signal output from control 46 causes the increase in motor speed to be dependent upon the flow-rate setting at the input to control 46. Finally, during repressurization, the control 46 receives a signal from a compressability compensation control 52 which causes control 46 to provide a signal to control 42 to cause an increase in motor speed for a period to compensate for the mechanical elasticity of the system components as a function of system flow-rate and pressure. The repressurization period is defined from the end of the refill period to a time during the delivery stroke of the piston as determined by the repressurization signal provided by motor control interface 30. The flow-rate control 46 additionally includes a linearity adjustment 47 for controlling system response over a wide range of flow settings.

In response to the above described signals provided by flow-rate control 46, the output signal from control 42 represents a signal indicative of desired motor speed. This signal is coupled to a servo amplifier 54 which in turn produces a high frequency signal proportional to desired motor speed. That signal is coupled through a power amplifier 58 to a motor drive circuit 60 to control the drive current to the motor 26 and therefore the speed of the pump during each part of the pump cycle.

In addition to the above control, the control 28 makes provisions for the control of motor speed and shutdown during various fault conditions caused by operation of the pump head. A first circuit includes an output from amplifier 58 which represents average motor current which, in turn, is proportional to pump head pressure. The output from amplifier 58 is coupled to overcurrent control 56 to inhibit delivery of a motor speed signal to the motor drive circuits when the average motor current exceeds a predetermined value. This circuit causes the motor to slow down until the average current falls below the set value thereby providing electrical protection and a limit on the maximum head pressure that may be developed by the pump.

A second circuit, including elements 62, 64, 66 and 70, acts to provide a control signal responsive to torque during the delivery portion of the pump cycle, to provide alarm and motor shutdown during over-torque conditions. In this example, the torque detector 62 is coupled to sense the armature current of motor 26 as a signal proportional to pump pressure. Detector 62 is designed to compensate for static friction in the armature to provide a more accurate indication of torque. In addition, torque compensation 70 is coupled to detector 62 to compensate for parasitic frictional torque known as windage friction. Since the effects of windage friction are greater at increased armature speed, the compensation provided by 70 is controlled to be responsive to the flow-rate setting at control 46.

The output from detector 62 is coupled to sample gate 64 which passes the signal to a torque limit sensing circuit 66. The circuit 66 in turn provides an output signal when the sensed torque is above set limits. This signal is provided to the motor control interface 30 to provide alarm and motor shutdown signals, and to the control terminal of gate 64 to allow continuous torque sensing during fault conditions.

In order to restrict the sampling of the pressure signal at detector 62 to the delivery portion of the pump cycle, a gate control 68 receives signals from the compressability control 52 which inhibits the provision of a gating signal from amplifier 54. Accordingly, the sample gate 64 will not pass the signal from detector 62 to the sensing circuit 66 until the refill and repressurization time periods have passed unless there is an over-torque condition indicated by the output at sensing circuit 66.

Figure 3:
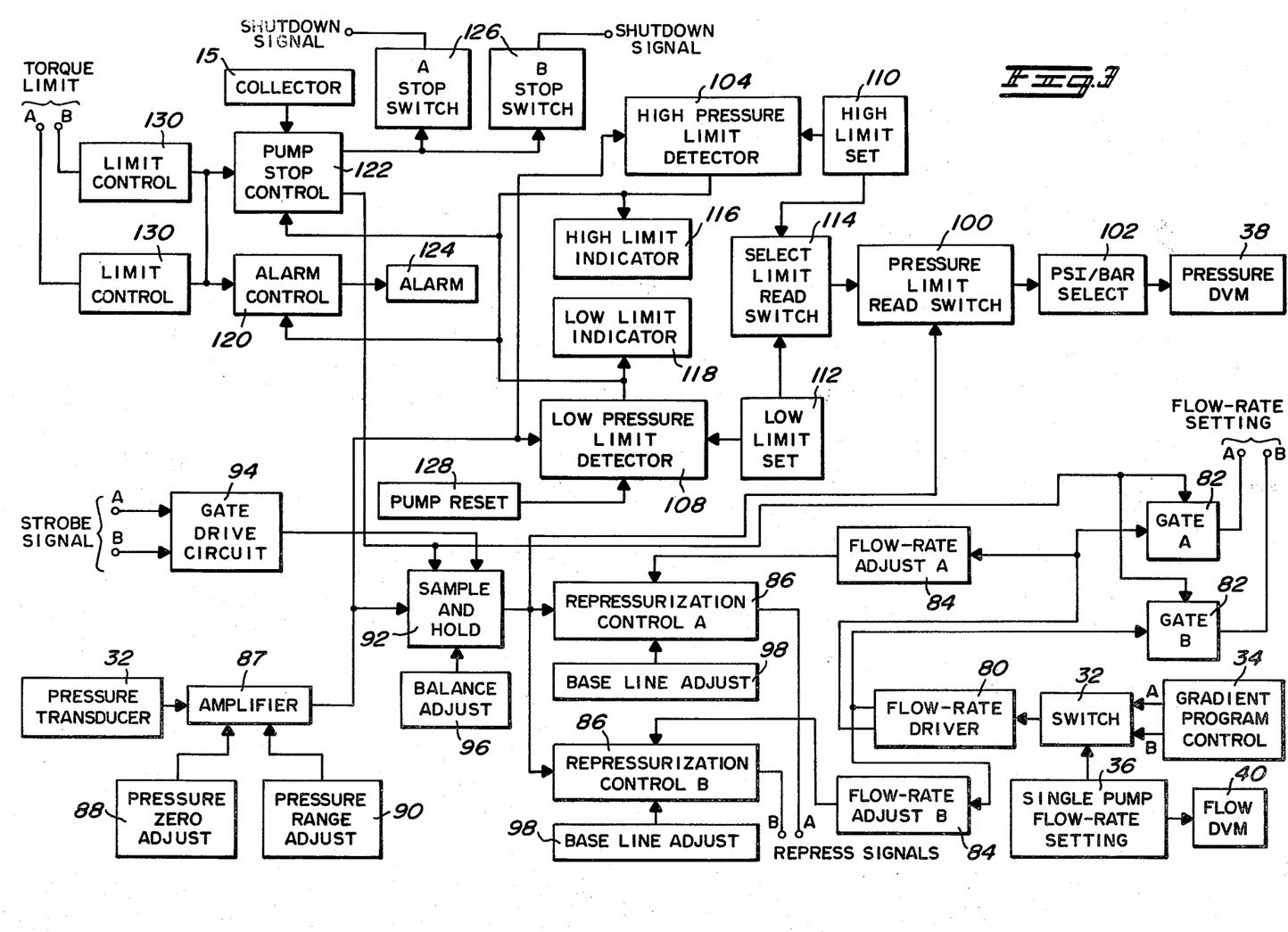
FIG. 3 is a block diagram schematically showing the functional operation of the motor control interface shown in FIG. 1.

Referring now to FIG. 3, a block diagram shows the functional operation of the motor control interface 30 as generally depicted in FIG. 1. The motor control interface 30 provides the flow-rate settings for pumps A and B to control pump speed, and also generates the repressurization signal for controlling the period of pump speed up during repressurization. The motor control interface 30 also provides for the sensing of pressure and the establishment of high and low pressure limits for controlling alarm and pump shutdown circuits.

Generally, the flow-rate settings are provided by gradient program control 34 for a two-pump gradient system and by single pump flow-rate setting 36 for a single-pump configuration. In the single pump mode, the flow-rate is read directly from the digital voltmeter 40 coupled to receive the flow-rate setting from 36. Switch 32 controls the mode of operation by selecting either of the signals from 34 or 36. As can be seen, when the gradient mode is employed, signals are developed for both the A and B pump circuits which include identical circuit elements. For purposes of simplicity, therefore, the motor control interface 30 will be described with reference to the operation of only one pump, it being understood that the same description applies to those elements for control of the second pump in the gradient mode.

With reference to FIG. 3, the flow-rate signal is coupled through a flow-rate driver 80 to provide a flow-rate setting signal to gates 82. Unless a pump stop signal is present to inhibit gate 82, the same provides the flow-rate setting to the flow-rate control 46 (FIG. 2) of the appropriate pump for setting the desired pump speed during the delivery stroke. The flow-rate setting is also coupled through a flow adjust circuit 84 to provide an adjustable output proportional to the flow-rate setting. The output from adjust 84 is then coupled to a repressurization control 86 which, in conjunction with a pressure signal, produces the repressurization signal coupled as input to compressability control 52 in FIG. 2.

The noted pressure signal is derived by sensing the pressure in the conduit 12 (FIG. 1) with pressure transducer 32, which in the preferred embodiment is a switch. The output of transducer 32 is coupled through amplifier 87 to provide a signal representing pressure. A pressure zero adjust 88 is coupled to calibrate amplifier 87 so that there is zero output at zero pressure. A pressure range adjust 90 is also coupled to the amplifier 87 to alter the responsive pressure range.

The output of the amplifier 87 provides a pressure signal to sample and hold 92 which provides a smoothed output representing pressure during the delivery portion of the pump cycle only. This is accomplished by providing a strobe signal to the control gage of sample and hold 92 to inhibit pressure sensing during refill and repressurization. The strobe signal is provided at the output of compensation control 52 (FIG. 2) and coupled to the gate of sample and hold 92 via gate drive circuit 94.

The smoothed pressure signal is coupled as the second input to repressurization control 86 for developing the repressurization signal. The control 86 combines the pressure and flow-rate signals to produce a repressurization signal which compensates for compressability based on flow-rate and actual delivery pressure. A baseline adjust 98 is provided to develop an adjustable pressure-flow baseline level with respect to which pulsation compensation can be provided. While the adjust 84 allows the circuit to compensate for pulsation over a wide range of flow-rates, the same are set to limit the maximum repressurization interval during operation in the gradient mode. This is to prevent the gate of sample and hold 92 from being strobed constantly off during certain pump operating conditions.

In addition to pulse compensation control, the motor control interface 30 provides for output pressure display and over and under pressure limit detection and display. Such pressure is read by coupling the smoothed pressure output from the sample and hold 92 to a pressure limit read switch 100. In one position the switch 100 couples the pressure signal to a PSI/BAR calibration select switch 102 which in turn provides the pressure signal to pressure digital voltmeter 38. The calibration select switch 102 allows the reading of delivery pressure in either pounds per square inch (PSI) or atmospheres (BAR).

In order to provide high and low limit pressure detection for alarm and motor shutdown control, the actual output pressure from amplifier 87 is coupled to high and low pressure limit detectors 104 and 108 respectively. The detectors 104 and 108 are constructed to produce an output signal at pressures above and below those set by high and low limit sets 110 and 112. The limit sets 110 and 112 accurately fix a signal representative of the pressure at which it is desired to stop the pump. The limit sets are also coupled to a select limit read switch 114 which allows either the high or low limit setting to be coupled to the digital voltmeter 38 in order to display the pressure limits.

When the pressure indicated by the signal from amplifier 87 falls below the low limit set or rises above the high limit set, the respective outputs of detectors 104 and 108 provide a signal which enables high and low limit indicators 116 or 118. At the same time, the respective outputs are coupled as input to alarm control 120 and pump stop control 122. These control circuits in turn provide signals which initiate alarm 124 and pump stop switches 126 to produce pump shutdown signals to flow-rate control 46 (FIG. 2). In connection with the low limit pressure indication, a pump reset 128 is coupled to detector 108 to allow the pump to be restarted following shutdown due to a low pressure fault.

As was described with reference to FIG. 2, the torque signal from sensing circuit 66 is provided to the motor control interface 30 via limit control 130. The output of the limit control couples a signal to the alarm control 120 and pump stop control 122 upon occurrence of an over-torque condition. As a result, the system responds to both instantaneous pressure and torque (from sensing circuit 66) to shutdown the system upon fault detection.

As can be seen with reference to FIG. 3, the output from the pump stop control 122 is coupled to sample and hold circuit 92 and gates 82 to provide additional circuit protection. Thus, when the pump stop signal is received at sample and hold 92, the circuit will produce a continuous output pressure signal representing actual pressure to be displayed by the digital voltmeter 38. At the same time, the signal will insure that the pumps stop by inhibiting gates 82 to prevent flow-rate signal delivery to control 46 (FIG. 2) during fault conditions.

As was noted with reference to FIG. 1, the sample changer 15 can additionally be used to provide automatic system operation. In the desired embodiment, the changer 15 is constructed to provide an output signal to the pump stop control 122 in the motor control interface 30 after the last vial in the rack is injected. At that time, the pumps will be stopped without an alarm indication until the rack is reset for subsequent operation.

In order to produce the functions and control described with reference to FIGS. 1–3, more detailed illustrations of exemplary circuits are shown in FIGS. 4A, 4B, 5A and 5B. It is to be understood, however, that the particular circuits are only examples of those that could be used to accomplish the functions and results described herein. In regard to the motor control circuit 28 as particularly shown in FIGS. 4A and 4B, the same was derived by modification of well-known control circuitry. Thus, the elements and values used in such circuitry are the same as included in prior art circuits except where modified in accordance with the present invention as indicated herein.

Figure 4A:
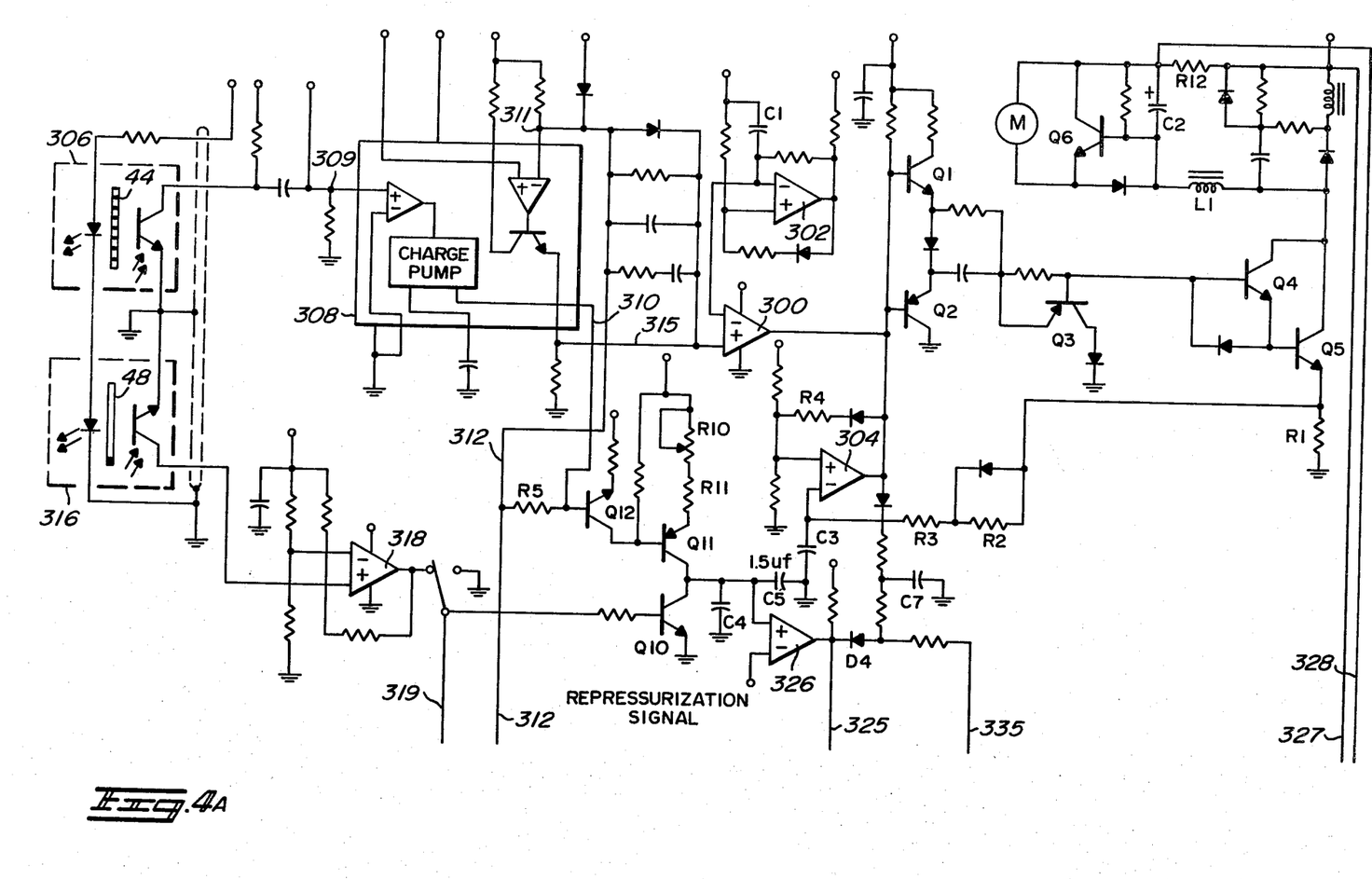
FIG. 4A and 4B is a detailed diagram showing exemplary circuits forming the motor control of FIG. 2.
Figure 4B:
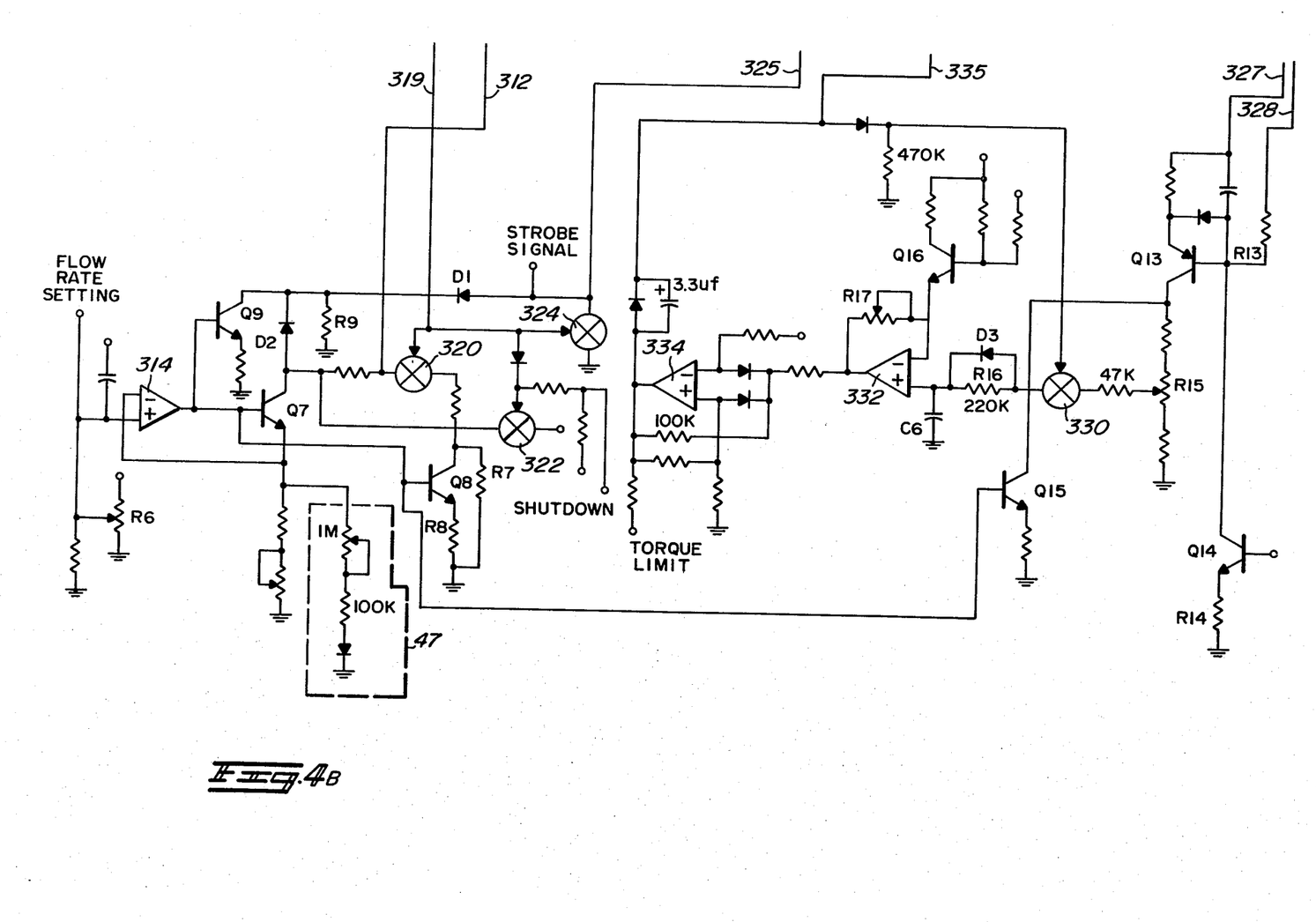

Turning first to FIGS. 4A and 4B, a detailed example of the servo circuitry of motor control 28 is illustrated. Referring first to the servo amplifier 54 of FIG. 2, the same is constructed from a differential comparator 300 (FIG. 4A) having the signal from the pump speed control 42 supplied to the non-inverting input. The inverting input is swept by a triangular waveform generated at capacitor C1 by the oscillator 302. In the present instance the circuit is constructed to have a frequency of about 20 KHZ with a voltage range of 7.5 to 11 volts. In operation, when the voltage at the non-inverting input to comparator 300 exceeds the minimum value of the triangular wave at the inverting input, an output pulse train is produced at the frequency of the triangular wave having a duty factor which increases from zero to 100% as the voltage at the non-inverting input increases. Thus, a drive signal is supplied to the power amplifier 58 (FIG. 2) where it is amplified by transistors Q1 and Q2 current limited by transistor Q3 and amplified to suitably high power level by transistors Q4 and Q5. Current through the collector of Q4 and Q5 establishes an average current in the motor driven circuit 60 (FIG. 2) through inductor L1 and capacitor C2 which controls motor speed. In order to insure that the motor will slow down when the turn on time of the transistors Q4 and Q5 rapidly decreases, the transistor Q6 is coupled to short the motor windings when voltage on C2 falls below the back emf of the motor. Since the +terminal of C2 and the motor are tied together, when the back emf exceeds the voltage on the capacitor by about 1.3 volts Q6 turns on and shorts the motor to decelerate the same in a well-known manner.

In order to provide for over-current protection, the current pulse train flowing through R1 is sensed through resistors R2 and R3 to charge capacitor C3 of over-current control 56. If the average motor current (as represented by the current pulse train) exceeds a predetermined limit, the comparator 304 clamps the bases of transistors Q1 and Q2 to ground thereby inhibiting any further signal input to amplifier 58. Since this also stops current flow through R1, capacitor C3 will discharge through R1 until its value falls below the hysteresis level set by R4 at which time, comparator 304 will remove the clamps on Q1 and Q2. In operation, the circuit acts to oscillate at a high frequency to provide switching mode current limiting which provides electrical protection as well as a limit for maximum motor torque representing maximum pump head pressure.

In developing the speed control signal supplied to servo amplifier 54 by the pump speed control 42, the tachometer disc 44 (FIG. 2) on the motor shaft is coupled to an optical transducer 306 to produce an AC output signal proportional to the speed of the armature. This AC signal is coupled to an LM2709 frequency-to-voltage converter 308 which produces square-topped output current pulses (having a pulse height and width independent of input frequency) at the rate of 2 pulses at the output 310 for each input cycle at input 309. The average current output therefore increases with increasing frequency because the duty factor tends toward 100% as the frequency approaches one-half of the output pulse width.

The pulse output from 310 is supplied through resistor R5 to a current summing node at input 311 of converter 308. An output current signal from control 46 representing the desired pump rate is also supplied to the summing node through line 312. The signal from control 46 is derived from a current source formed by comparator 314 and transistor Q7 (FIG. 4B) which provides a current through the collector of Q7 proportional to the flow-rate setting supplied to the non-inverting input of comparator 314. When the two signals at the summing node are combined, the resulting output at line 315 is a signal indicative of the desired motor speed during the delivery stroke which is supplied to the non-inverting input of 300 for motor control as was previously described. Resistor R6 provides an adjustment which allows the output of comparator 314 to be set to insure that the motor stops at zero flow-rate in spite of any off-set or leakage currents in the circuits.

In order to provide for pulse compensation, the disc 48 (FIG. 2) on the motor cam shaft is mechanically coupled to refill period control 50. The disc consists of an optical flag phased on the cam shaft so that the leading edge coincides with the top dead center of the cam (beginning of refill stroke) and has an angular length equal to the refill return angular length of the cam. The flag interrupts an optical signal in a conventional optical transducer 316 to produce a high output from comparator 318 during the refill period. This output is then coupled through line 319 to flow-rate control 46 and compressability control 52 to control motor speed during refill and repressurization.

In connection with the control 46, the high output from comparator 318 is coupled to the control terminal of analog gates 320 and 322 (FIG. 4B). At this time, gate 320 connects the current source transistor Q8 and resistor R7 to the summing node to produce an output signal from control 46 which speeds up the drive motor during refill. Since the base of transistor Q8 is coupled to the output of comparator 314 to control collector conduction in accordance with flow-rate setting, R7 will cause motor speed up at low set points while Q8 will cause motor speed up at high set points due to current flow through R8. At the same time, the gate 322 clamps the collector of Q7 to 7.5 volts during the duration of the refill cycle.

In connection with the control 52 of FIG. 2, the high output from comparator 318 (FIG. 4A) is coupled to the control pin of analog gate 324 (FIG. 4B) clamping the output 325 of differential comparator 326 to ground. At the same time, the same high signal is coupled to the base of transistor Q10 discharging capacitors C4 and C5 to ground. The capacitors C4 and C5 are coupled to the non-inverting input of comparator 326 while the repressurization signal from interface 30 is coupled to the inverting input. During refill, the low at the output of comparator 326 enables repressurization current source transistor Q9 and resistor R9 but does not cause further motor speed up due to the clamp of 7.5 volts on the collector Q7 through gate 322.

At the end of the refill part of the cycle, the repressurization part of the cycle begins as the piston starts to advance. At this time, the optical flag causes the output from comparator 318 to go low turning Q10 off and allowing voltage rise on C4 and C5. The voltage rise on C4 and C5 is made proportional to the angle of cam shaft rotation past bottom dead center (end of refill stroke) by charging through R10 and R11 in the emitter of Q11. The proportionality is established by driving the transistor combination Q11, Q12 with the average voltage across R5 which is in turn proportional to motor speed as represented by the pulse output from line 310 of the converter 308. The proportional voltage causes the current at the collector of Q11 to be proportional to the instantaneous angular velocity of the motor armature. C4 and C5 thereafter integrate this current to produce a voltage proportional to angular rotation of the armature past bottom dead center of the cam.

During the initial repressurization interval, the voltage at the non-inverting terminal of comparator 326 is less than the repressurization voltage provided to the inverting input terminal causing the output of comparator 326 to be low. At this time diodes D1 and D2 enable Q9 and R9 to carry current from the summing node 311 of the converter 308 to speed up the motor. The amount of motor speed-up tracks the set point speed fixed by the flow-rate setting since the base of Q9 is controlled by the output of amplifier 314. The duration of the repressurization speed up, expressed in the angular amount of speed-up shaft rotation, is made proportional to an adjustable pressure/flow baseline level and provide pulse compensation with respect to flow-rate and an accurate pressure as will be described with reference to the motor control interface 30.

In order to provide torque limit detection for the delivery part of the cycle, the output torque is derived by monitoring the armature current with detector 62 through lines 327 and 238 as was described with reference to FIG. 2. In the detector 62, transistor Q13 (FIG. 4B) develops a collector current proportional to the voltage drop across R12 in the motor drive circuit 60 which in turn is proportional to the armature current and dependent on motor torque. Due to various amounts of static friction in the armature, the armature current is greater than zero while the motor is rotating with zero output torque. A resistor R13 is therefore incorporated along with transistor Q14 and R14 to cause a voltage drop across resistor R13 to compensate for this error. The output current in the collector of Q13 is then coupled through R15 to produce a voltage signal proportional to motor torque. To overcome the effect of a parasitic frictional torque that increases with armature speed (windage friction), a transistor Q15 is used to drain off a portion of the current through Q13. The collector current of Q15 is made proportiional to the flow-rate setting (pump speed) by coupling its base to the output of amplifier 314 to allow increased compensation at increased speeds.

The output signal from detector 62 is coupled to an analog gate 330 which controls application of the signal to a sample and hold capacitor C6 through the resistor R16 and diode D3 combination. This voltage is coupled through operational amplifier 332 having a resistor R17 coupled to allow zeroing of the output of amplifier 332 at zero output torque. The adjustment R17 is coupled to a current source at Q16 to enable zeroing adjustment rather than a change of the gain of the operational amplifier.

The signal output from amplifier 332 is coupled to an over-torque limit circuit incorporating comparator 334. In operation the output of comparator 334 is normally low until the output of amplifier 332 exceeds an upper limit set by comparator 334 at which time it goes high. The output high is provided to the motor control interface 30 to initiate alarm and motor shutdown and as input to the control terminal of gate 330 to cause continuous torque sensing during an over-torque condition.

The analog gate 330 is also controlled by signals received from the servo amplifier 54 through control gate 68 to remain on during the delivery stroke. Control gate 68 includes diode D4 which causes a voltage from the capacitor C7 to be coupled to the control terminal of gate 330 through line 335 during the delivery stroke. During refill, however, when the signal from the comparator 318 clamps the output of comparator 326 to ground, the capacitor C7 discharges to ground through diode D4 thereby inhibiting gate 330 during refill unless an over-torque output signal from comparator 334 is present.

Figure 5A:
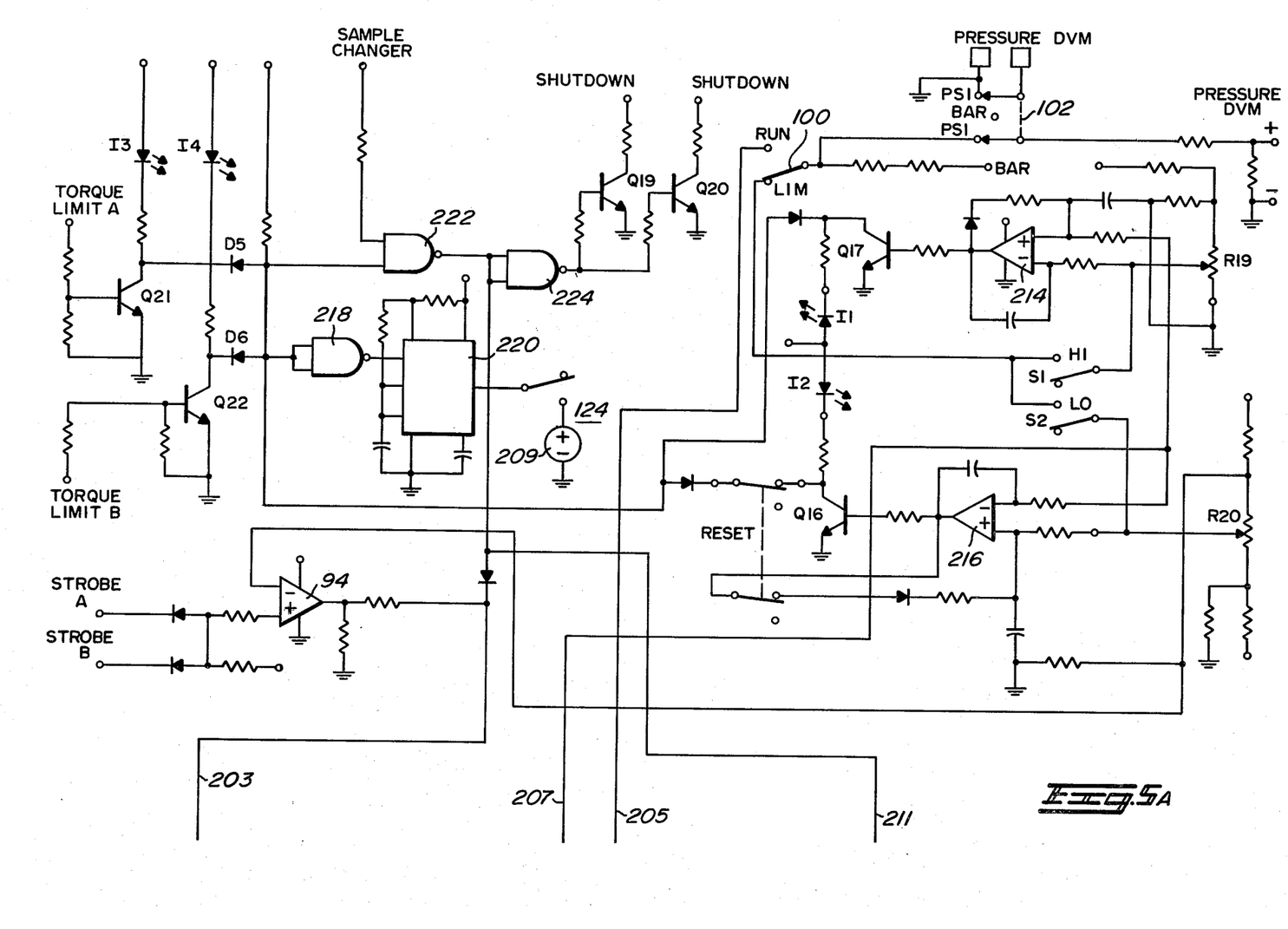
FIG. 5A and 5B is a detailed diagram showing exemplary circuits forming the motor control interface of FIG. 3.
Figure 5B:
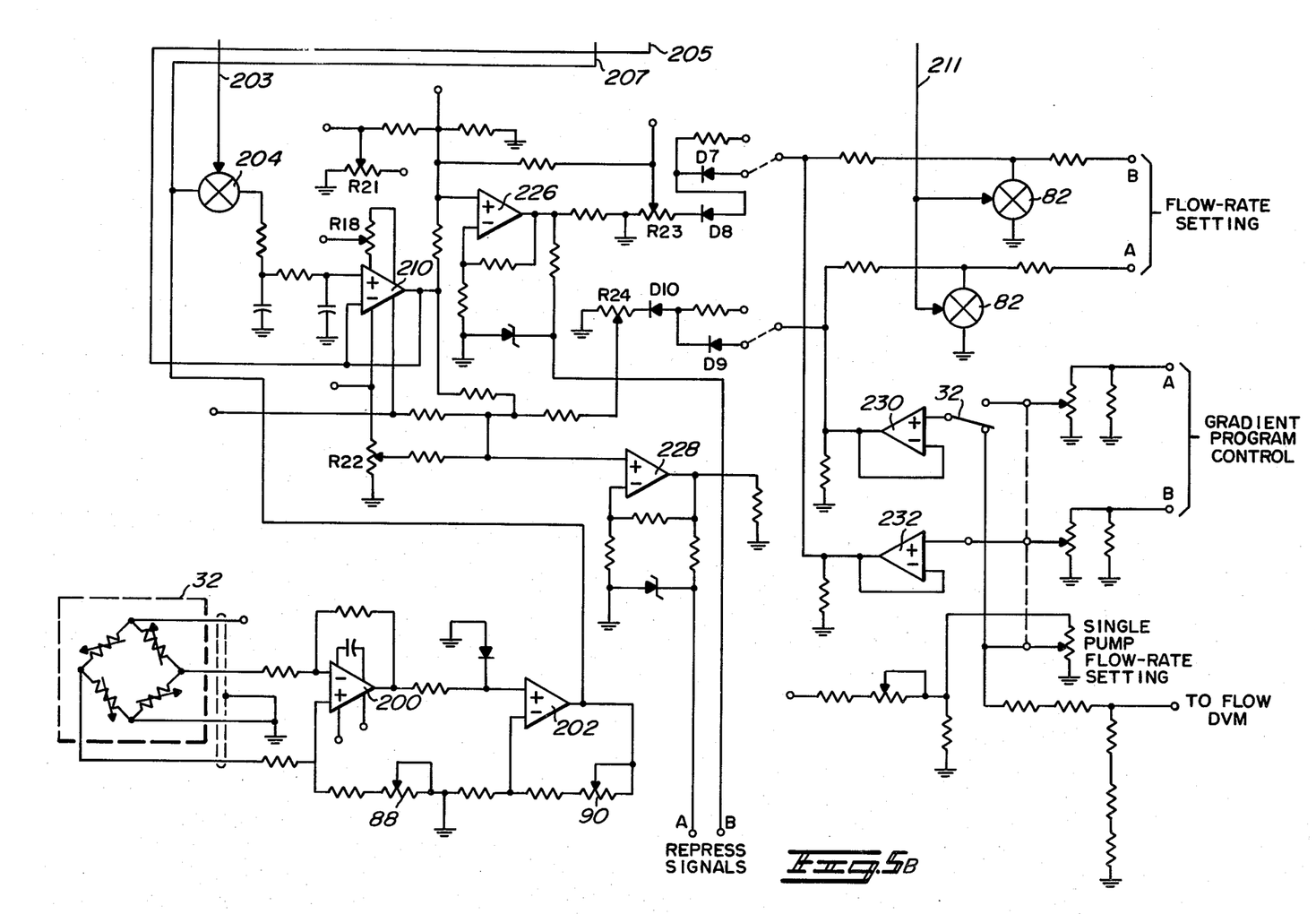

Referring now to FIGS. 5A and 5B, the pressure transducer 32 consists of a four arm strain gage mounted on the back of a pressure sensing diaphragm. Its differential output voltage representing operating pressure is amplified by amplifier 87 (FIG. 3) consisting of differential amplifiers 200 and 202 (FIG. 5B) having zero adjust and pressure range adjust potentiometers 88 and 90 to provide a zero output at zero pressure and an adjustment for pressure range. The pressure signal at the output of the amplifier 87 is coupled as input to sample and hold circuit 92 consisting of analog gate 204 and the amplifier 210. The gate 204 has its control terminal coupled through line 203 to receive a strobe signal via the gate drive circuit 94 from the compensation control 52 to inhibit the gate during refill and repressurization. As a result of this sampling, the output of the sample and hold circuit 92 produces a value indicative of the delivery pressure only which is a smoothed pressure signal (due to the removal of pulsations caused by refill and repressurization). A balance adjustment is provided by R18 to enable the output of the sample and hold to be set at zero volts when the output of the amplifier 87 is zero.

The output of the sample and hold circuit 92 is coupled through line 205 to switch 100 (FIG. 5A) which allows system pressure to be read on the digital voltmeter 38. As was previously noted, the PSI/BAR switch 102 allow calibration of the DVM to enable reading of the pressure in pounds per square inch or atmosphere.

The actual pressure from the output of amplifier 87 is coupled through line 207 to high and low pressure limit detectors 104 and 108. The high limit detector generally includes comparator 214 and transistor Q17 while the low limit detector includes comparator 216 and transistor Q16. The high and low limit sets are generally constructed from potentiometers R19 and R20, respectively, providing voltage reference levels to the designated inputs of 214 and 216, respectively. The voltage reference levels are also coupled through switches S1 and S2 forming the select limit read switch 114 to enable the levels to be read individually on the pressure DVM.

In operation, when an over or under pressure signal is received at the inputs to 214 and 216, the appropriate comparator will cause the base of one of the transistors Q17 or Q16 to turn on causing current flow in the appropriate collector. At that time, current flow will cause the appropriate indicator lights I1 or I2 to light and also cause a low to appear at the inputs of NAND gate 218 of the alarm control 120. The NAND gate will produce a high output to the circuit 220 which in turn will initiate an audio alarm 124.

The low signals from the output of the limit detectors 104 and 108 are also coupled to the pump stop control 122 which includes NAND gates 222 and 224. The high output from NAND gate 222 is coupled to NAND gate 224 to provide a low output signal to pump switches 126 formed by transistors Q19 and Q20 to provide motor shutdown signals to gate 322. This signal causes the collector of transistor Q7 to be clamped to 7.5 volts thereby stopping the motor.

The over-torquue limit signal from the output of comparator 334 in FIG. 4B is also coupled to provide a control signal to the alarm and pump shutdown circuits via limit controls 130. Limit controls 130 includes transistors Q21 and Q22 which receiver the high signal output from comparator 334 at their respective bases. The collectors, upon receipt of the high signal, short the voltage through diodes D5 and D6 to ground to produce a low at the input of the alarm and pump stop control circuits. At the same time, a current path is completed to light indicator lamp I3 and I4 to identify the particular pump in the over-torque condition. Since it is possible for motor torque in the pump to build up to a dangerous amount without a corresponding pressure increase sensed by the pressure transducer 32 (as when the pump head filter is plugged) the above circuitry provides a safety cutoff and an indication of the faulty pump.

If it is desired to employ automatic operation under the control of the sample changer 15, a low signal from the sample changer 15 should be provided as a second input to the pump stop control NAND gate 222. This produces a stop signal upon termination of system operation but does not cause an alarm indication.

The high output from the NAND gate 222 of the pump stop circuit 122, which occurs during a fault condition, is coupled through lines 207 and 203 to the control terminals of the analog gate 204 (FIG. 5B) in sample and hold 92. This causes the circuit 92 to continuously read actual pressure during a fault condition. At the same time, the stop signal is provided via line 211 to gates 82 to inhibit flow-rate signal passage to the control 46 as was previously described with reference to FIG. 3.

As has been previously mentioned, improved pulsation compensation is provided in the present circuit by developing a repressurization signal which compensates with respect to flow-rate and pressure. With respect to present circuit, the repressurization signal is developed by providing the smoothed pressure signal and a flow-rate signal to summing amplifiers 226 and 228. Resistors R21 and R22, forming baseline adjustors 98, provide an adjustable baseline offset potential to compensate properly for residual pulsations at low pressures and low flows.

The flow-rate signals used to form the other inputs to controls 86 are provided at the output of drive amplifiers 230 and 232 forming the flow-rate driver 80. Such signals are selected from the single pump flow-rate setting 36 or gradient program 34 as have been previously described. The flow-rate setting is then coupled through the appropriate flow adjustments 84, which include diodes D7–D10 and potentiometers R23 and R24, to the summing input at the non-inverting terminal of amplifiers 226 and 228 in the control circuits 86. The signal at the output of each summing amplifier represents a repressurization signal for delivery to the corresponding compensation control 52, which compensates with respect to the flow-rate and pressure from an adjustable pressure/flow baseline. The potentiometers R23 and R24 provide an adjustable compensation for flow and in cooperation with the diodes D7–D10 allows improved tracking of pulsation compensation with respect to flow-rate variations.

In operation, the compensation control 52 provides a repressurization limit that is increased by the incorporation of capacitor C5 which allows increasing the maximum angular rotation of the pump during the compensated repressurization interval over that of the prior art. This allows each pump to be essentially flat-compensated over the flow-rate range. In a gradient chromatograph operating in the "flow" gradient mode (both pumps increasing in speed during the operation of a gradient program), however, a high flow-rate and high pressure can develop at the end of the program. Accordingly, while maximum repressurization compensation (maximum repressurization interval) is desired, the two pumps could cause system malfunction by strobing off the sample and hold gate 204 continuously if the pumps were turning at the same speed and were 180° out of phase. Thus, the maximum repressurization interval is limited by the flow-rate adjustments 84 to prevent such a condition while allowing improved compensation to the maximum practical extent.

In accordance with the above circuits, improved pulsation compensation is provided which prevents the output flow-rate from dropping off at high flow-rates. This is accomplished since the actual cyclical flow delivery interval is not as greatly preempted by the actual repressurization interval as occurred in prior art compensation circuitry. For this reason much less linearity compensation is also needed and the linearity adjustments 47 are therefore able to be much less sensitive. Such linearity adjustments can thus be made with high resistance potentiometers 47 coupled in the emitter circuit of Q7 in FIG. 4A.

It should be noted that while the detailed circuits of FIGS. 5A and 5B have not included specific values and an identification of the elements chosen to form the circuits, the same are selected in accordance with normal design practices to provide proper biasing and signal levels to perform the functions indicated and to interface with the voltage levels of the particular apparatus and circuitry with which the control interface may be employed. In addition, the elements may be selected from a variety of prior art devices capable of accomplishing the functions described as would be apparent to one of ordinary skill in the art. Thus, any values and specifically illustrated elements are only considered exemplary of the operable circuitry that may be employed in the practice of the present invention. Obviously, many other modifications and variations of the invention are possible in light of the above teachings. It is therefore to be understood that within the scope of the appended claims, the invention may be practiced otherwise than as specifically described.

What is claimed is:

1. A circuit for compensating for pulsations in pump flow-rate by controlling pump motor speed during delivery, refill, and repressurization periods of a pump cycle comprising:

a first pump driven by a first motor;

means for providing at least one signal representing pump flow-rate;

first motor control means coupled to said motor and responsive to said flow-rate signal for driving the first motor at a speed proportional to said flow-rate signal during the delivery period of the pump cycle and at an increased speed during the refill and repressurization periods of the pump cycle; and interface control means coupled to said motor control means and responsive to said flow-rate signal for providing a repressurization signal causing the first motor control means to increase motor speed during repressurization for a time period proportional to the magnitude of the repressurization signal.

2. The circuit of claim 1 wherein said interface control means includes:

means for providing a signal representing pump pressure;

sample and hold means coupled to sample said pressure signal during the delivery portion of a pump cycle for providing a delivery pressure signal; and
summing means coupled to sum said delivery pressure signal and said flow-rate signal to produce said repressurization signal.

3. The circuit of claim 1 wherein said interface control means further includes means for adjusting the magnitude of the repressurization signal relative to a baseline level.

4. The circuit of claim 1 wherein said interface means includes a flow-rate adjust means for adjusting the tracking and varying the magnitude of the flow-rate signal.

5. The circuit of claim 4 wherein said interface control means further includes:
high limit set means for providing a first reference signal;
low limit set means for providing a second reference signal;
high pressure detector means coupled to receive said pressure signal and said first reference signal for providing an output signal when said pressure signal exceeds said first reference signal;
low pressure detector means coupled to receive said pressure signal and said second reference signal for providing an output signal when said pressure signal is less than said second reference signal; and
alarm control means coupled to said high and low pressure detector means for providing an alarm signal upon receipt of an output signal from either of said detector means.

6. The circuit of claim 1 further including:
a second pump driven by a second motor;
a second motor control means coupled to said second motor and responsive to a flow-rate signal for driving the second pump motor at a speed proportional to the flow-rate signal during the delivery period of the pump cycle and at an increased speed during the refill and repressurization periods of the pump cycle, and wherein said means for providing at least one flow-rate signal includes:
a single pump flow-rate setting means for providing a single flow-rate signal; and
gradient program control means for providing programmable first and second flow-rate signals, and further wherein said interface control means includes:
first repressurization control means coupled to said first motor control means and responsive to an input signal for providing a first repressurization signal causing the first motor control means to increase motor speed during repressurization for a time period proportional to the magnitude of the first repressurization signal; and
second repressurization control means coupled to said second motor control means and responsive to an input signal for providing a second repressurization signal causing the second motor control means to increase motor speed during repressurization for a time period proportional to the magnitude of the second repressurization signal; and
switch means for selectively coupling the single pump flow-rate signal to the first motor control means and as the input signal to said first means in one switch position and the first and second flow-rate signals to the first and second motor control means respectively and as the input signals to said first and second means respectively in a second switch position.

7. The circuit of claim 6 wherein said interface control means further includes:
means for providing a signal representing pump pressure;
sample and hold means coupled to sample said pressure signal during the delivery portion of a pump cycle for providing a delivery pressure signal; and
wherein said first and second repressurization means each include:
summing means coupled to sum said delivery pressure signal and its associated flow-rate signal to produce said repressurization signal.

8. The circuit of claim 7 wherein each of said summing means includes means for adjusting the magnitude of the repressurization signal relative to a baseline level.

9. The circuit of claim 7 wherein said interface control means further includes:
a first flow-rate adjust means for tracking and varying the magnitude of the first flow-rate signal; and
a second flow-rate adjust means for tracking and varying the magnitude of the second flow-rate signal.

10. The circuit of claim 7 wherein said interface control means further includes:
high limit set means for providing a first reference signal;
low limit set means for providing a second reference signal;
high pressure detector means coupled to receive said pressure signal and said first reference signal for providing an output signal when said pressure signal exceeds said first reference signal;
low pressure detector means coupled to receive said pressure signal and said second reference signal for providing an output signal when said pressure signal is less than said second reference signal; and
alarm control means coupled to said high and low pressure detector means for providing an alarm signal upon receipt of an output signal from either of said detector means.

11. The circuit of claim 10 wherein said interface control means further includes:
select limit switch means coupled to said high and low limit set means for selectively providing one of said first or second reference signals as an output;
pressure limit read switch means coupled to receive said delivery pressure signal and the output of said select limit switch means for selectively providing an output of one of those signals; and
a digital voltmeter coupled to the output of said pressure limit read switch means in order to display a value proportional to the pressure signal of the first or second reference signals.

12. The circuit of claim 11 wherein each motor control means further includes:
torque detector means coupled to its respective motor for sensing motor armature current and providing a signal representing motor torque;
means responsive to said torque signal for providing a torque limit output signal when the motor torque signal exceeds a predetermined value, and wherein said interface control means further includes:
first limit control means responsive to the torque limit output signal from said first motor control means for providing an output signal when the first motor torque signal exceeds said predetermined value;

second limit control means responsive to the torque limit output signal from said second motor control means for providing an output signal when the second motor torque signal exceeds said predetermined value; and said alarm means being coupled to said first and second limit control means for providing an alarm signal upon receipt of an output signal from either of said limit control means.

13. The circuit of claim 12 wherein each of said first and second limit control means includes an indicator means for providing a visual indication of a pump fault condition in response to the receipt of a torque limit output signal.

14. The circuit of claim 12 wherein said interface control means further includes:
a pump stop control means coupled to said first and second limit control means and said high and low detector means for providing a pump stop signal upon receipt of an output signal from any of said limit control means and detector means;
stop switch means coupled to said pump stop control means for providing shutdown signals upon receipt of a pump stop signal, and wherein each of said motor control means further includes:
means responsive to a shutdown signal for causing the motor to stop.

15. The circuit of claim 14 wherein said interface control means further includes:
first gate means coupled to said pump stop control means for preventing said first motor control means from receiving a flow-rate signal upon receipt of a pump stop signal; and
second gate means coupled to said pump stop control means for preventing said second motor control means from receiving a flow-rate signal upon receipt of a pump stop signal.

16. The circuit of claim 14 wherein said sample and hold means is coupled to be responsive to said pump stop signal to provide the pressure signal as the delivery pressure signal upon the occurrence of a pump stop signal.

17. The circuit of claim 7 wherein each motor control means further includes:
means for providing a strobe signal during the refill and repressurization periods of the pump cycle, and wherein said interface control means further includes:
gate drive circuit means for providing an output signal upon receipt of a strobe signal from either motor control means; and
said sample and hold means being coupled to be responsive to the output signal from said gate drive circuit means to prevent sampling of the pressure signal during refill and repressurization.

18. In a chromatographic system including a chromatographic means providing a stationary phase, a conduit coupled to supply a mobile phase to said stationary phase, first and second fluid reservoirs, a pump coupled to each reservoir to supply fluid from that reservoir to said conduit, a motor coupled to drive each pump, and means for controlling motor speed during delivery, refill and repressurization of each pump cycle to reduce pulsations in the system flow-rate, the improvement in said means for controlling comprising:
means for providing at least one signal representing pump flow-rate;
motor control means coupled to each pump motor and responsive to the flow-rate signal for driving the associated motor at a speed proportional to the flow-rate signal during the delivery period of the pump cycle and at an increased speed during the refill and repressurization periods of the pump cycle; and
interface control means coupled to said motor control means and responsive to at least one flow-rate input signal for providing at least one repressurization signal causing at least one of said motor control means to increase motor speed during repressurization for a time period proportional to the magnitude of the repressurization signal.

19. The system of claim 18 wherein means for providing at least one flow-rate signal includes:
a single pump flow-rate setting means for providing a single flow-rate signal; and
gradient program control means for providing programmable first and second flow-rate signals, and wherein said interface control means includes;
first repressurization control means coupled to one of said motor control means and responsive to an input signal for providing a first repressurization signal causing the one of said motor control means to increase motor speed during repressurization for a time period proportional to the magnitude of the first repressurization signal; and
second repressurization control means coupled to the other of said motor control means and responsive to an input signal for providing a second repressurization signal causing the other of said motor control means to increase motor speed during repressurization for a time period proportional to the magnitude of second repressurization signal; and
switch means for selectively coupling the single flow-rate signal as the input signal to the motor control means and first repressurization control means in one switch portion and the first and second flow-rate signals as the input signals to respective ones of said motor control means and the first and second repressurization control means in a second switch position.

20. The system of claim 19 wherein the improvement further comprises:
a pressure transducer coupled to sense the pressure in the conduit supplying the mobile phase, and wherein the interface control means further includes:
amplifier means coupled to said pressure transducer for providing a signal proportional to actual pressure;
sample and hold means coupled to said amplifier means to sample said pressure signal during the delivery portion of a pump cycle for providing a delivery pressure signal, and wherein said first and second repressurization control means each include:
summing means coupled to sum said delivery pressure signal and its associated flow-rate signal to produce said repressurization signal.

21. The system of claim 20 wherein each of said summing means includes means for adjusting the magnitude of the repressurization signal relative to a baseline level.

22. The system of claim 20 wherein said interface control means further includes:
a first flow-rate adjust means for tracking and varying the magnitude of the first flow-rate signal; and a second flow-rate adjust means for tracking and varying the magnitude of the second flow-rate signal.

23. The system of claim 20 wherein said interface control means further includes means responsive to said pressure signal for providing an alarm signal when said pressure signal is greater than a first reference signal or less than a second reference signal.

24. The system of claim 23 wherein said means for providing an alarm signal comprises:

high limit set means for providing a first reference signal;

low limit set means for providing a second reference signal;

high pressure detector means coupled to said amplifier means and said high limit set means for providing an output signal when said pressure signal exceeds said first reference signal;

low pressure detector means coupled to said amplifier means and said low limit set means for providing an output signal when said pressure signal is less than said second reference signal; and alarm control means coupled to said high and low pressure detector means for providing said alarm signal upon receipt of an output signal from either of said detector means.

25. The system of claim 24 wherein said interface control means further includes:

separate indicator means coupled to each detector means for providing a visual indication of a pressure fault upon receipt of an output signal from said detector means.

26. The system of claim 20 wherein each of said motor control means includes:

means for sensing motor torque and providing a torque limit signal when said motor torque exceeds a predetermined value, and wherein said interface control means further includes:

means responsive to said torque limit control signal for providing a pump stop signal; and means responsive to said pump stop signal for causing each of said motor control means to stop the pump motors upon the occurrence of a torque fault condition.

* * * * *

UNITED STATES PATENT AND TRADEMARK OFFICE
CERTIFICATE OF CORRECTION

PATENT NO. : 4,225,290
DATED : September 30, 1980
INVENTOR(S) : Robert W. Allington It is certified that error appears in the above-identified patent and that said Letters Patent are hereby corrected as shown below:

IN THE ABSTRACT:

Line 14, change "flow rate" to "flow-rate".

IN THE SPECIFICATION:

Column 1, line 57, after the word "provide", insert "adequate".

Column 9, line 17, change "driven" to "drive".

Column 11, line 18, change "238" to "328".

Signed and Sealed this

Third Day of February 1981

[SEAL]

Attest:

RENE D. TEGTMEYER

Attesting Officer     Acting Commissioner of Patents and Trademarks